United States Patent
Raducanu et al.

(10) Patent No.: US 10,624,547 B2
(45) Date of Patent: Apr. 21, 2020

(54) SENSING DEVICE WITH ARRAY OF MICROELECTRODES

(71) Applicants: IMEC VZW, Leuven (BE); Katholieke Universiteit Leuven, KU LEUVEN R&D, Leuven (BE)

(72) Inventors: Bogdan Raducanu, Ramnicu Valcea (RO); Srinjoy Mitra, Leuven (BE); Refet Firat Yazicioglu, Herent (BE)

(73) Assignees: IMEC VZW, Leuven (BE); Katholieke Univesiteit Leuven, KU LEUVEN R&D, Leuven (BE)

( * ) Notice: Subject to any disclaimer, the term of this patent is extended or adjusted under 35 U.S.C. 154(b) by 529 days.

(21) Appl. No.: 15/197,778

(22) Filed: Jun. 30, 2016

(65) Prior Publication Data
US 2017/0000368 A1 Jan. 5, 2017

(30) Foreign Application Priority Data
Jun. 30, 2015 (EP) ..................... 15174610

(51) Int. Cl.
*A61B 5/0478* (2006.01)
*A61B 5/04* (2006.01)
(Continued)

(52) U.S. Cl.
CPC ........ *A61B 5/04001* (2013.01); *A61B 5/0478* (2013.01); *A61B 5/6868* (2013.01);
(Continued)

(58) Field of Classification Search
CPC .......................... A61B 5/04001; A61B 5/0478
See application file for complete search history.

(56) References Cited

U.S. PATENT DOCUMENTS 6,171,239 B1 * 1/2001 Humphrey ........... A61B 5/0482
  600/372
8,229,539 B1 * 7/2012 Motoyoshi ......... A61B 5/04001
  600/378
(Continued)

FOREIGN PATENT DOCUMENTS

WO     2012/018631 A2    2/2012

OTHER PUBLICATIONS

European Search Report, European Patent Application No. 15174610.4, dated Oct. 16, 2016, 7 pages.
(Continued)

*Primary Examiner* — Lee S Cohen
(74) *Attorney, Agent, or Firm* — McDonnell Boehnen Hulbert & Berghoss LLLP

(57) ABSTRACT

Devices and systems described herein relate to a sensing device that includes an output area and an electrode area. The output area includes an output circuit comprising an integrator adapted to integrate a received current so as to generate an output voltage corresponding to the received current. The electrode area includes an electrode comprising an exposed, electrically conductive, surface area and electrode circuitry connected to the exposed surface area. The electrode circuitry comprises a voltage-to-current transducer adapted to produce a wire current corresponding to a voltage present at the exposed surface area. The sensing device also includes a connecting wire electrically connecting the electrode circuitry to the output circuit, wherein the current received by the output circuit is the wire current.

17 Claims, 6 Drawing Sheets

(51) Int. Cl.
*A61B 5/00* (2006.01)
*A61N 1/05* (2006.01)

(52) U.S. Cl.
CPC .......... *A61B 5/7225* (2013.01); *A61B 5/4076* (2013.01); *A61B 2562/043* (2013.01); *A61N 1/0529* (2013.01); *A61N 1/0551* (2013.01)

(56) References Cited

U.S. PATENT DOCUMENTS

| | | | | |
|---|---|---|---|---|
| 8,934,965 | B2* | 1/2015 | Rogers | A61B 5/0478 600/378 |
| 9,070,492 | B2* | 6/2015 | Yarmush | A61B 5/04001 |
| 2004/0006264 | A1* | 1/2004 | Mojarradi | A61B 5/0478 600/378 |
| 2004/0249302 | A1* | 12/2004 | Donoghue | A61B 5/04001 600/544 |
| 2009/0292336 | A1 | 11/2009 | Nishida et al. | |
| 2010/0081958 | A1* | 4/2010 | She | A61B 5/0031 600/544 |
| 2013/0072775 | A1 | 3/2013 | Rogers et al. | |
| 2013/0079615 | A1* | 3/2013 | Yoon | A61B 5/04001 600/377 |
| 2014/0276151 | A1* | 9/2014 | Xi | A61B 5/029 600/508 |
| 2015/0313501 | A1* | 11/2015 | Shachar | A61B 34/73 600/374 |
| 2016/0143591 | A1* | 5/2016 | Bracke | A61B 5/7203 600/373 |
| 2016/0278713 | A1* | 9/2016 | Shoaran | A61B 5/7232 |

OTHER PUBLICATIONS

Viventi, Jonathan et al., "Flexible, Foldable, Actively Multiplexed, High-Density Electrode Array for Mapping Brain Activity In Vivo", Nature Neuroscience, vol. 14, No. 12, Nov. 13, 2011, pp. 1599-1605.

Khodagholy, Dion et al., "In Vivo Recordings of Brain Activity Using Organic Transistors", Nature Communications, vol. 4, Mar. 12, 2013, pp. 1-7.

Lopez, Carolina Mora et al., "An Implantable 455-Active-Electrode 52-Channel CMOS Neural Probe", IEEE Journal of Solid-State Circuits, vol. 49, No. 1, Jan. 2014, pp. 1-14.

Tateno, Takashi et al., "A CMOS IC-Based Multisite Measuring System for Stimulation and Recording in Neural Preparations In Vitro", Frontiers in Neuroengineering, vol. 7, Article 39, Oct. 2014, pp. 1-23.

Shulyzki, Ruslana et al., "320-Channel Active Probe for High-Resolution Neuromonitoring and Responsive Neurostimulation", IEEE Transaction on Biomedical Circuits and Systems, Jun. 2014, pp. 1- 16.

Seidl, Karsten et al., "CMOS-Based High Density Silicon Microprobe Arrays for Electronic Depth Control in Intracortical Neural Recording", Journal of Microelectronmechanical Systems, vol. 20, No. 6, Dec. 2011, pp. 1439-1448.

* cited by examiner

SENSING DEVICE WITH ARRAY OF MICROELECTRODES

CROSS-REFERENCE TO RELATED APPLICATIONS

The present application is a non-provisional patent application claiming priority to European Patent Application No. EP 15174610.4, filed Jun. 30, 2015, the contents of which are hereby incorporated by reference.

FIELD OF THE DISCLOSURE

This invention relates generally to the field of biosensors, and more specifically to sensing devices comprising an array of microelectrodes for the analysis of tissue and/or neuroscience experimentation.

BACKGROUND

Devices with microelectrode arrays for bio-sensing purposes have an important role in the areas of diagnostic such brain monitoring or in vitro cell monitoring. Conventional microelectrode sensing arrays may include, for example, neural probes, which are used to measure neural activity at one or more sites of the brain.

Conventional neural probes comprise a probe base and a shank, the shank extending from the base for insertion into a portion of the brain. In some cases, electrodes are disposed along the length of the shank, each electrode being adapted to measure a voltage, corresponding to neural activity, in the immediate vicinity of the electrode. In use, the probe base may be positioned on the outside of the brain and comprises base circuitry suitable for recording voltages present at the electrodes of the shank. The base circuitry may further comprise further processing circuitry, for example, a filter or digitization circuitry.

A neural probe will usually comprise shank wires positioned in the shank and connecting an electrode to the base circuitry. As the width of the shank is generally extremely narrow, to reduce potential damage to the brain, there is a maximum limit on the number of shank wires that may be in a shank. This is due to the physical limitations in positioning shank wires, the difficulty in fabricating sufficiently small shank wires and possible complications due to capacitive coupling between closely spaced shank wires.

It is clear that a limitation on shank wires induces a proportional limit on the allowable number of electrodes that may be permitted on the available area for the electrodes. However, it is desirable to allow the electrode area to have an increased number of electrodes in order to acquire more information from regions near to that electrode area. A similar problem arises when implementing a very high density two-dimensional microelectrode arrays which can be conceived as rows of one-dimensional shank. A microelectrode array of this kind, with very limited space between the rows, will also have limited number of wires to carry the signal to a base area placed outside the array.

SUMMARY

The invention is defined by the claims.

According to an exemplary embodiment, there is provided a sensing device comprising: an output area having an output circuit comprising an integrator adapted to integrate a received current so as to generate an output voltage corresponding to the received current; an electrode area comprising: an electrode comprising an exposed, electrically conductive, surface area and electrode circuitry connected to the exposed surface area, wherein the electrode circuitry comprises a voltage-to-current transducer adapted to produce a wire current corresponding to a voltage present at the exposed surface area; and a connecting wire electrically connecting the electrode circuitry to the output circuit, wherein the current received by the output circuit is the wire current.

According to an exemplary embodiment, there is provided a sensing device adapted to detect a voltage level in a site of biological tissue. A voltage level at an exposed surface area of an electrode placed at a desired site of the biological tissue (e.g. a brain or a heart) is converted to a current level by electrode circuitry, before being passed along a connecting wire to output circuitry located in an output area of the voltage sensing apparatus. The output circuitry comprises means for converting the wire current along the connecting wire back into an output voltage, such that the output voltage produced by the output circuitry corresponds to the voltage detected by the associated electrode.

An exposed surface area of an electrode may, for example, be in electrical contact with a portion of biological tissue (e.g. a brain, a heart, a liver, lungs, muscles etc.) so as to measure a voltage present in that portion. It will be understood that an exposed surface area of the electrode measures or conducts a voltage in the immediate vicinity of the exposed surface area.

According to an exemplary embodiment, the voltage measured at the exposed surface area of the electrode (a detected voltage) is converted into a corresponding (e.g. proportional) current by electrode circuitry, comprising a transducer, connected to the exposed surface area. The current is passed along a connected wire connected at a first end to the electrode circuitry and at a second end to the output circuitry, positioned in an output area of the output circuitry.

According to an exemplary embodiment, the output circuitry is adapted to convert the current along the connecting wire to an output voltage corresponding (e.g. proportional) to the voltage at the electrode. Such output circuitry comprises an integrator adapted to integrate the current along the connecting wire so as to generate the output voltage. The integrator may, in at least one embodiment, comprise a capacitor and/or a transistor and/or an operational amplifier.

According to an exemplary embodiment, the integrator may reduce high frequency noise by averaging the current over time. Integrating the current in this manner thereby reduces the need for pre-filtering of the signal (i.e. at the electrode circuitry), at least partially avoiding the need for filtering circuitry at the electrode to thereby reduce power consumption and the area required for circuitry at the electrode (i.e. the required footprint of the electrode). Reduced power consumption at the electrode reduces the heat dissipation at the electrode, thereby reducing the temperature that proximate biological tissue is heated. A reduced electrode area allows for miniaturization of electrode circuitry thereby reducing the size of the voltage sensing apparatus. Furthermore, a reduced electrode area permits an increased number of electrodes to be positioned within a given area.

According to an exemplary embodiment, a gain of the detected voltage is applied based on at least the integration time of the integrator, thereby also allowing the dynamic adjusting of gain to be effected (for example by changing the integration time).

In exemplary embodiments, there may be a plurality of connecting wires each carrying a wire current to be integrated at an associated output circuitry. In such embodiments, it may be understood that each connecting wire is held at substantially the same voltage with differing current levels (corresponding to different detected voltages). This may provide reduced cross-talk due to capacitive coupling between two or more connecting wires.

Due to the reduction in capacitive coupling, a sensing device according to an exemplary embodiment may thereby allow for the provision of connecting wires placed more closely together than in previous or conventional voltage sensing apparatus. This may allow for an increased number of connecting wires (and hence electrodes) in the electrode area of a voltage sensing apparatus.

Using a current mode transmission according to an embodiment allows for the reduction and/or mitigation of the effects caused by the electrical resistance of the connecting wires in the electrode area. This has the effect of improving the accuracy of the readout and increasing the available bandwidth of the voltage sensing apparatus compared to a typical voltage transmission. Eliminating such adverse effects caused by the connecting wire allows for miniaturization of the wire size, reducing the size of the connecting wire(s) and/or allowing for increased wire density.

According to an exemplary embodiment, the voltage-to-current transducer comprises a field-effect transistor having a gate, a drain and a source, wherein: the gate of the transistor is connected to the exposed surface area; one of the drain or the source of the transistor is held at a first predetermined voltage level, such that a voltage at the gate of the transistor causes a corresponding wire current to flow at the other one of the drain or the source of the transistor. It should be understood that the gate of the transistor need not be directly connected to the exposed surface area, but may by connected via additional circuit components, for example a decoupling capacitor.

Hence there may be provided a single-transistor transducer, which may provide low power consumption and footprint (i.e. the area that the electrode circuitry takes up). The above suggested configuration allows isolation of the exposed surface area, such that the voltage detected is not influenced by a load resistance of the electrode or output circuitry.

An exemplary integrator may comprise a integrating capacitor having a first and second plate, the integrating capacitor being arranged so that the wire current is integrated at the first plate of the integrating capacitor to thereby generate an output voltage at the first plate, and the second plate of the integrating capacitor is held at a ground voltage; and a controllable reset switch connected between the first plate of the integrating capacitor and the second plate so as to controllably reset the output voltage.

According to an embodiment, the wire current may be integrated in the output circuitry at a first plate of an integrating capacitor, the second plate of the integrating capacitor being connected to a ground voltage. Integrating the wire current at the first plate allows the voltage across the capacitor to increase over time. To reset the capacitor (i.e. bring the first plate back to a ground voltage) a reset switch may span between the two plates of the capacitor, and when active, may cause the first plate of the capacitor to be grounded.

Optionally, the electrode further comprises a high-pass filter connected between the exposed surface area and the electrode circuitry. In an example embodiment, the high-pass filter is a passive high-pass filter.

Provision of a high pass filter prior to the electrode circuitry limits the very low frequency artifacts, such as low frequency noise or DC biasing, that may saturate the electrode circuitry.

The electrode circuitry may further comprise an electrode buffer transistor adapted to buffer the current produced by the voltage-to-current transducer.

According to an exemplary embodiment, the wire current may be buffered through an electrode buffer transistor before being provided to the connecting wire. Buffering the wire current ensures separation between the electrode circuitry (for example, the voltage-to-current transducer) and possible voltage ripples present at the output of the electrode circuitry caused by the changing state of the switches. Furthermore, such an arrangement (alternatively named a cascade) provides improved an input-output isolation, higher input impedance and a higher frequency bandwidth. According to an exemplary embodiment, this may result in improving the fidelity, linearity and performance of the sensing apparatus.

In one exemplary embodiment, the electrode area comprises a plurality of electrodes, the plurality of electrodes being divided into at least two sets of electrodes, each set of electrodes comprising at least two electrodes; and a plurality of connecting wires, each connecting wire being associated with a single set of electrodes and connectable to each electrode in that set of electrodes, wherein the wire current from each electrode in a set of electrodes is multiplexed using time-division multiplexing onto the associated connecting wire.

According to an exemplary embodiment, there may be provided a plurality of connecting wires, each connecting wire having a plurality of wire currents multiplexed thereon. Multiplexing in such a manner allows a plurality of electrodes to be associated with a single connecting wire, such that the total number of connecting wires in the electrode area may be reduced relative to a normal or conventional voltage sensing apparatus (where each connecting wire is associated with a single electrode). Similarly, an increased number of electrodes may be provided when the number of connecting wires is limited.

Time-division multiplexing may introduce high-frequency noise, for example noise fold-back or aliasing. This may be mitigated by the present invention through provision of the integrator in the output circuitry, which permits reduction of such high-frequency noise. In such an exemplary embodiment, the output area optionally comprises a plurality of output circuits, each output circuit being connected to a different connecting wire.

In comparison to conventional devices, wherein each electrode is associated with a respective connecting wire and a respective output circuit, present embodiments include connection of an output circuit to a plurality of electrodes (via a connecting wire). In an example embodiment, the overall size of the output circuit associated with any given electrode has less constraint (i.e. the footprint of each output circuit may be made larger), which may allow larger components to be used for limiting noise, for example, thermal noise.

Furthermore, each output circuit may comprise a plurality of sampling circuits, each sampling circuit being associated with a different electrode from the set of electrodes associated with the connected connecting wire, wherein each sampling circuit is adapted to sample and hold the output voltage corresponding to the associated electrode.

According to an exemplary embodiment, there may be the same number of sampling circuits in connection with a given connecting wire (via further output circuitry) as there are electrodes, such that each sampling circuit may be associated with a single, different, electrode. Each sampling circuit may be controlled to only sample the voltage at the integrator (i.e. the output voltage) when the voltage at the integrator corresponds to the voltage detected at the electrode associated with the respective sampling circuit. The arrangement of sampling circuits may otherwise be thought to demultiplex the output voltage provided by the integrator.

In one exemplary embodiment, the electrode circuitry of each electrode optionally comprises: an output node at which the wire current is defined; a first controllable switch adapted to selectively connect the output node to the connecting wire; and a second controllable switch adapted to selectively connect the output node to a node held at a second predetermined voltage level. Optionally, the output node is always connected to the connecting wire or the node held at the second predetermined voltage level or both. In other words, the voltage-to-current transducer is never turned off, which at least partially eliminates issues concerning settling time.

The output circuit(s) may further comprise a wire buffer transistor and/or additional circuit components adapted to maintain the connecting wire at the second predetermined voltage level.

Maintaining the same voltage level at the connecting wire as at the node held at a second predetermined voltage level, such that the output of the electrode circuitry is switched between the same two voltage levels, at least partially avoids any possible switching noise (in the output circuitry for example) back propagating along the connecting wire to the electrode circuitry.

According to an embodiment, the electrode area optionally further comprises: a first plurality of control lines, each control line connected to control a respective first controllable switch in a single electrode from each set of different electrodes; and a second plurality of control lines, each control line connected to control a respective second controllable switch in a single electrode from each set of different electrodes. Thus, rather than each controllable switch of each electrode being controlled individually, a plurality of controllable switches of electrodes in different sets may be controlled in parallel. In other words, voltages detected by electrodes in different sets may be measured in parallel. In an example embodiment, a reduced number of control lines and hence a reduced number of wires required in the electrode area, may permit the size or width of the electrode area to be reducible.

In one exemplary embodiment the electrode area comprises at least one connecting wire, each connecting wire being connectable to no fewer than 2 unique electrodes. There may be a total of no less than 2 electrodes divided into sets of at least 2 electrodes each, each set of electrodes being connected to a different connecting wire.

The electrodes may be grouped in sets comprising any number of electrodes, for example, sets comprising at least 2 electrodes, for example, 8 or more electrodes per set, for example, 24 or more electrodes per set. It is noted that, the number of electrodes in each set need not be the same, such that each set of electrodes may comprise a different number of electrodes.

In one or more further exemplary embodiments, the number of control lines is proportional to the number of electrodes in any given set. For example, if each set of electrodes comprises 8 electrodes, there may be a multiple of 8 number of control lines (e.g. 16 control lines). Each control line may, for example, be adapted to control a respective switch of a respective electrode in each set (i.e. a single control line may control more than one electrode in different sets).

By way of example, each electrode may have a limited length, width and/or diameter of no more than 50 μm, for example, no more than 25 μm, for example no more than 10 μm. In other words, the footprint (i.e. the amount of surface area that the exposed surface area of a given electrode takes up) of each electrode is limited to a maximum predetermined area.

According to at least one embodiment of the invention, there may be provided a neural probe comprising a probe base and a shank directly coupled to the base. The electrode area may be formed in the shank, and the output area may be formed in the probe base. At least one electrode may be positioned on the exterior of the shank to permit the exposed surface area to be exposed. Connecting wires may run up the shank to connect the at least one electrode to the output circuitry positioned in the probe base.

The shank may be understood to be a narrow structure or protrusion adapted to be inserted into the brain to permit the detection of at least one voltage in the vicinity of the shank. By way of example only, the shank may be no more 250 μm thick, for example no more than 150 μm thick and, in some embodiments, no more than 50 μm thick.

A thin shank may lower the chances of damaging biological tissue, such as the brain in which the shank is inserted.

In another embodiment, there may be provided a biosensor comprising a flexible membrane; wherein the electrode area is formed on the flexible membrane. Such a flexible membrane may be positioned, for example, on an external surface of the brain so as to detect at least one voltage present at an exterior surface of the brain. An exemplary flexible membrane may comprise at least one of: polyester, polyimide and/or metallic foil.

BRIEF DESCRIPTION OF THE FIGURES

Examples embodiments will now be described in detail, with reference to the accompanying drawings, in which.

DETAILED DESCRIPTION

In the following, the word "comprising" does not exclude other elements or steps, and the indefinite article "a" or "an" does not exclude a plurality. The mere fact that certain measures are recited in mutually different embodiments does not indicate that a combination of these measures cannot be used to advantage. Any reference signs should not be construed as limiting the scope. In some exemplary embodiments described herein, the sensing device may be embodied as a neural probe. However, it will be clear to the skilled person that other sensing device embodiments may be implemented and useful for other types of in vivo or in vitro biological sensors (for example, a sensor comprising a flexible substrate upon which a plurality of electrodes of an electrode area is mounted).

Figure 1:
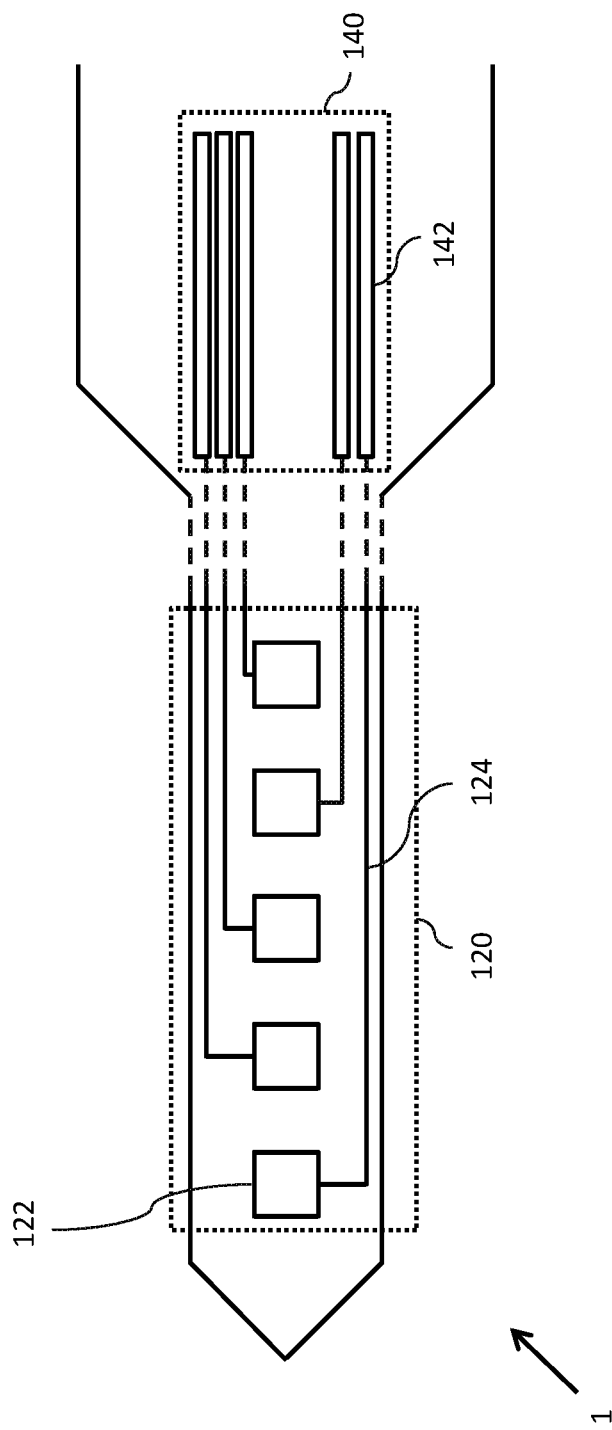
FIG. 1 illustrates a sensing device according to an exemplary embodiment.

FIG. 1 is illustrative of a sensing device 1 according to a first embodiment. The sensing device 1 comprises a shank portion, or electrode area, 120 and a base portion, or output circuitry area, 140 coupled together. Disposed along the shank is a plurality of electrodes, comprising at least a first electrode 122. Each electrode is at least partially exposed to the exterior of the shank 120. In the present embodiment, each electrode is associated with and electrically connected to a different base circuit positioned in the base 140. By way of example, the first electrode 122 is connected to a first base circuit 142. According to an exemplary embodiment the sensing device 1 may be a neural probe.

According to an embodiment, each electrode in the shank is connected to its respective base circuit in the base by a respective shank wire. For example, first electrode 122 is connected to the first base circuit 142 by way of a first connecting wire 124.

As indicated by the dashed lines, FIG. 1 is not necessarily to scale, and the shank 120 may rather be of an arbitrary length and width relative to the base 140.

Figure 2:
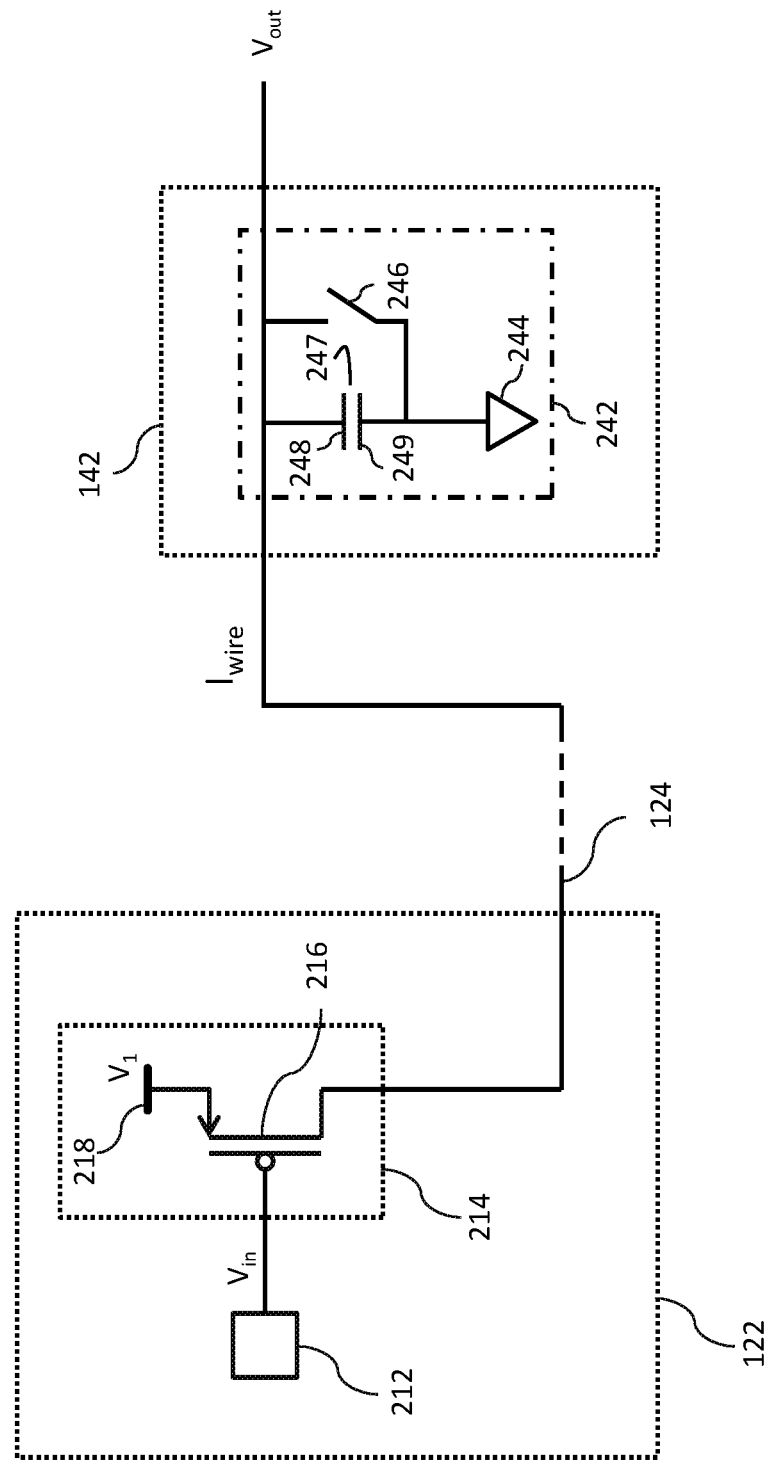
FIG. 2 illustrates a schematic of an electrical circuit of a portion of a sensing device according to an exemplary embodiment.

Turning to FIG. 2, a representative schematic of a portion of the sensing device 1 according to an exemplary embodiment is shown. Specifically, there is identified the first electrode 122 connected to the first base circuit 142 by the first connecting wire 124.

The electrode 122 comprises an exposed surface area 212 and electrode circuitry 214 connected together. The exposed surface area 212 comprises an electrically conductive contact (for example, a metal electrode) that, in use, is in contact with, for example, a portion of the region or tissue of interest so as to measure a voltage present in or at the region. This measured, input voltage $V_{in}$ is subsequently passed to the electrode circuitry. According to an exemplary embodiment, the region of interest is, for example, a portion of the brain.

In other words, the exposed surface area is positioned on the exterior surface of the shank 120. The electrode circuitry may be positioned beneath the exposed surface area, such that, in embodiments, the maximum footprint or area that the electrode circuitry may take up is bounded or defined by the size of the exposed surface area.

The electrode circuitry comprises a voltage-to-current transducer 214, adapted to convert the voltage detected by the exposed surface area 212 (the input voltage $V_{in}$) to a wire current $I_{wire}$. This wire current is passed along the first connecting wire 124 to the first base circuit 142. The first base circuit integrates the wire current $I_{wire}$ so as to generate an output voltage $V_{out}$ corresponding (e.g. proportional) to the input voltage $V_{in}$.

In the present embodiment, the voltage-to-current transducer comprises a field-effect transistor 216 (for example, a MOSFET), having a drain, a source and a gate. According to an exemplary embodiment, the field-effect transistor 216 is a P channel field-effect transistor. The gate of the field-effect transistor 216 is connected to the exposed surface area 212, such that the voltage detected by the exposed surface area $V_{in}$ is applied to the gate of the field effect transistor 216. In some embodiments, additional biasing circuits may be used to maintain the transistor at a suitable operating point (e.g. a quiescent point).

The source of the field effect transistor 216 is connected to a first node 218 held at a first predetermined voltage level $V_1$. It will be readily understood that as the voltage at the gate $V_{in}$ varies (according, for example, to a varying voltage level in the brain) so the current permitted to flow between the source and the drain of the transistor will vary. Accordingly, a wire current $I_{wire}$ corresponding to the voltage at the gate of the field effect transistor 216 (and thereby the voltage in a portion of the brain) may be generated.

In general, the wire current (i.e. the output of the voltage-to-current transducer) may be thought to be a combination of a continuous wire current (DC) and alternating wire current (AC), i.e. $I_{wire}=I_{wireDC}+i_{wireAC}$. $I_{wireDC}$ may be determined by a biasing circuit (if present) connected to the gate of the voltage-to-current transducer. The alternating current ($I_{wireAC}$) is dependent upon a transconductance gain ($g_m$) of the voltage-to-current transducer and the voltage detected by the exposed surface area $V_{in}$. This transconductance gain may, for example, be at least partially dependent on the biasing circuit.

The AC wire current $i_{wireAC}$ output by the voltage-to-current transducer may be modeled as:

$$I_{wireAC}=V_{in} \times g_m \qquad (1)$$

The first base circuit of the first embodiment comprises an integrator 242 adapted to perform the integration of a wire current $I_{wire}$ received from the first connecting wire 124 so as to generate an output voltage $V_{out}$ corresponding to the wire current $I_{wire}$ (and thereby the input voltage $V_{in}$).

According to an embodiment, the integrator 242 comprises an integrating capacitor 247 having a first plate 248 and a second plate 249. The first plate 248 is connected to receive the wire current $I_{wire}$ and the second plate 249 is held at a constant ground voltage supplied at a ground node 244. Provision of the wire current $I_{wire}$ to the first plate 248 between an initial, first point in time $t_0$ and a later, second point in time $t_1$ induces a build-up of charge (Q) at the first plate in accordance with the following equation:

$$Q(t)=\int_{t_0}^{t_1} I_{wire}(t)dt+Q(t_0) \qquad (2)$$

where $Q(t_0)$ is the initial charge at the first plate.

This may be further simplified under the assumption that the initial charge at the first plate is zero and the wire current may be modeled as a constant value:

$$Q=I_{wire} \times t \qquad (3)$$

wherein t is the difference in seconds between the later point in time $t_1$ and the initial point in time $t_0$ (i.e. an integration time t during which the current is integrated at the first plate of the capacitor).

There is a known relationship between capacitance of the integrating capacitor C, charge at the first plate of the integrating capacitor Q and voltage $V_{out}$ across the integrating capacitor (i.e. $Q=V_{out} \times C$). Thus the voltage across the integrating capacitor 247 (output voltage, $V_{out}$) changes over time in accordance with:

$$V_{out}(t) = \frac{1}{C}\int_{t_0}^{t_1} I_{wire}(t)dt + V_{out}(t_0) \qquad (4)$$

This may likewise be simplified, assuming that the initial charge at the first plate is zero (i.e. voltage across the capacitor is also zero) and the wire current is a constant value, as:

$$v_{out} = I_{wire} \times \frac{t}{C} = (V_{in}g_m + I_{wireDC}) \times \frac{t}{C} \quad (5)$$

Thus is can be readily seen that a voltage $V_{out}$ across the integrating capacitor 247 may be induced by the provision of a current to a first plate 248 of that integrating capacitor. It will be understood, therefore, that wire currents $I_{wire}$ of different magnitude cause a different output voltage $V_{out}$. Assuming that the continuous wire current $I_{wireDC}$ is constant (i.e. the voltage-to-current transducer is biased at the same voltage) so the alternating wire current $I_{wire}$ may be thought to control the output voltage.

It will be readily apparent that, disregarding the typically constant DC biasing component $I_{wireDC}$, there is a voltage gain (A) induced by the circuitry (i.e. gain is applied to the voltage $V_{in}$ detected at the exposed surface area):

$$A = g_m \frac{t}{C} \quad (6)$$

Thus it will be seen that the gain of the circuitry in the sensing device may be adjusted by altering the integration time t that the first plate 248 of the capacitor 247 is exposed to the wire current $I_{wire}$. In one exemplary embodiment, the integration time is sufficiently small to permit sampling of voltage output signals at a frequency high enough to capture the complete bandwidth of the signal of interest. By way of example, an exemplary integration time might be chosen that allows detection of signals having a frequency of no more than 20 kHz, for example, at least 40 kHz.

The gain A is dependent on the capacitance of the integrating capacitor 247, thus an integrating capacitor having a lower capacitance may provide a higher gain in some embodiments. That being said, a lower value of capacitance of the integrating capacitor increases the noise and therefore decreases the accuracy of the output voltage (due to Johnson-Nyquist Noise or thermal noise). Thus a compromise may have to be made between achieving sufficient gain, and acceptable signal-to-noise ratio.

By way of example, the gain A of the circuitry may be adjusted to be no less than 1, for example 10, for example, 20. A higher gain value (for example, greater than 10) may reduce the performance constraint of optional subsequent amplification stages.

The integrating circuit may be otherwise thought to behave as a low pass circuit, attenuating signals of frequencies above 1/t. In embodiments t is chosen to maximize attenuation of typically unwanted high frequency noise, while the, typically more useful low frequency, signal passes unaffected.

The above equations 1-6 are merely representative models of the ideal circuit for the sake of clarity, and do not take into account, for example, any possible source impedance (e.g. of the electrode circuitry) and assume a linear charging of the capacitor. It will be readily understood by the skilled person that additional circuits may be present in order to correct for such non idealities and/or insure proper continuous current (DC) biasing of the circuit without departing from the scope of the invention.

There may be provided a reset switch 246 connected across the plates 248, 249 of the capacitor 247 so as to selectively connect the first plate 248 to the ground node 244. This essentially resets the first plate, bringing the output voltage to a ground voltage; that is bringing the capacitor back to a 'zero initial conditions' state. It will be understood that this permits sampling of the output voltage $V_{out}$ to be taken, as the switch may successively connect and disconnect the first plate of the capacitor to the second plate (and hence to a ground voltage).

Figure 3:
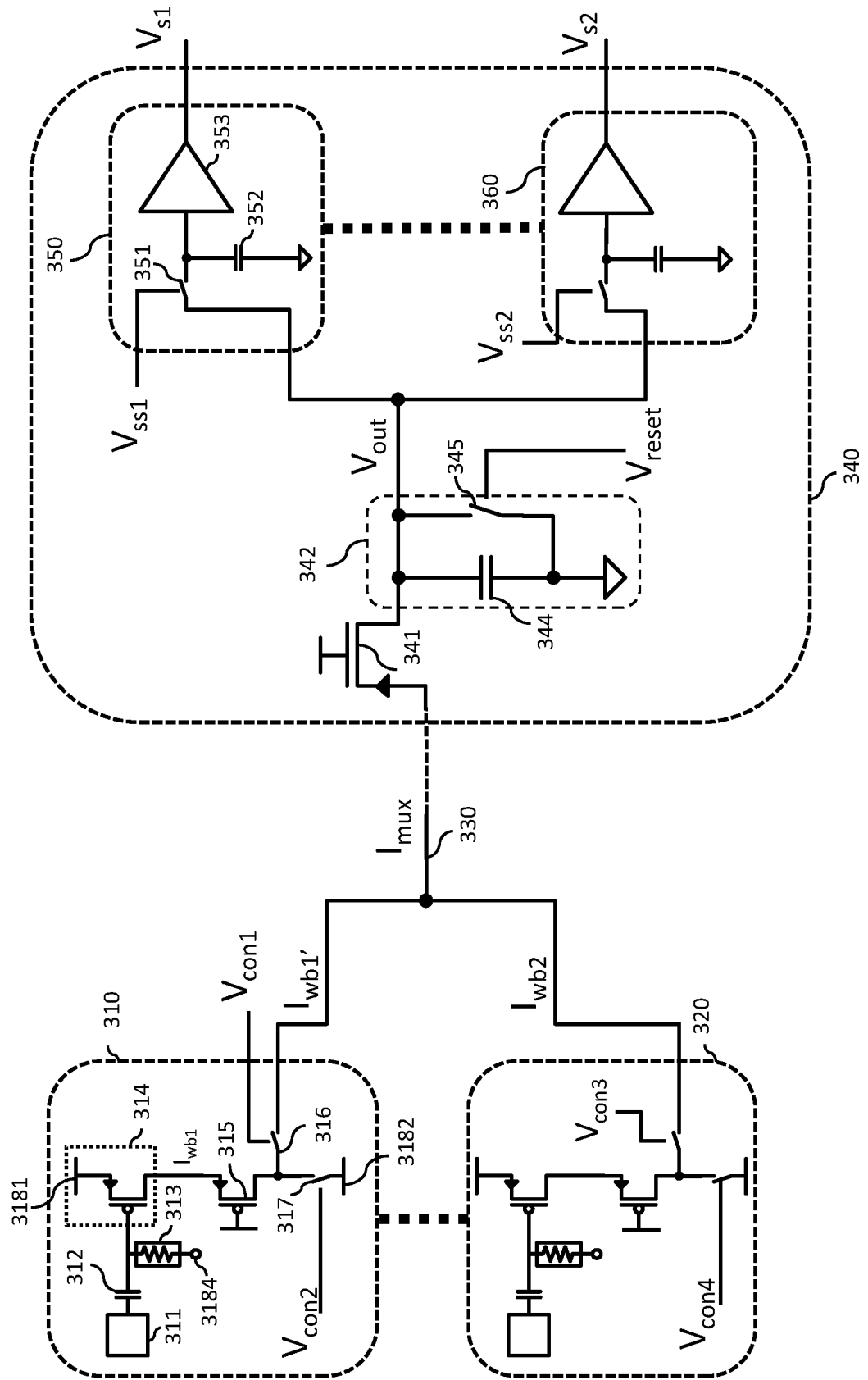
FIG. 3 depicts a schematic of an electrical circuit of a sensing device according to an exemplary embodiment.

A representative schematic of a portion of a sensing device according to a second embodiment is shown in FIG. 3. In this second embodiment, there is shown a plurality of electrodes (for example, first electrode 310 and second electrode 320) each adapted to measure a voltage, for example, in a respective portion of the brain.

Each electrode may produces a respective wire current (first wire current $I_{wb1'}$ and second wire current $I_{wb2}$). These wire currents are multiplexed, using an example method of time division multiplexing, onto a connecting wire 330 to produce a multiplexed wire current $I_{mux}$. This multiplexed wire current $I_{mux}$ is passed by the connecting wire 330 to base circuitry 340 for further processing.

It will be readily understood that although only two electrodes are identified in the present embodiment, any number of electrodes (for example, 8 electrodes or 16 electrodes or more) may be multiplexed onto a single connecting wire without departing from the scope of the invention.

The features and characteristics of the first electrode 310 shall be hereafter described. The second electrode 320 (and any further electrode not shown) are configured in substantially the same arrangement and shall be not described for the purposes of conciseness and clarity.

Similar to the electrode described with reference to the first embodiment, the first electrode 310 comprises both an electrically conductive exposed surface area 311 and a voltage-to-current transducer 314. The voltage-to-current transducer 314 is adapted to generate a current corresponding to a voltage detected at the exposed surface area 311, and may be embodied as previously described with reference to the previous voltage-to-current transducer 214.

Disposed between the exposed surface area 311 and the voltage-to-current transducer 314 is a high pass filter 312, 313. The high pass filter 312, 313 is embodied as a standard passive first-order high pass filter having a filter capacitor 312 and a filter resistor 313 connected at one end to a filter node 3184 held at a voltage level $V_b$, to bias the circuit at a proper DC point. Provision of the high pass filter may provide a reduction of the very low frequency artifacts (i.e. low frequency noise or DC biasing) that may saturate the electrode circuitry, for example the voltage-to-current transducer 314.

In exemplary embodiments, the capacitance of the filter capacitor 312 is extremely small (e.g. <1 pf), but the resistance of the filter resistor sufficiently large (e.g. >1 G$\Omega$) so as to achieve a relatively low corner frequency of the high-pass filter. In one exemplary embodiment, this corner frequency is less than 10 Hz, in other embodiments, the corner frequency of the high pass filter is less than 1 Hz.

Positioned to receive current produced by the voltage-to-current transducer 314 is an electrode buffer transistor 315 adapted to buffer the current to output a buffered wire current $I_{wb1'}$. According to an embodiment, where the voltage-to-current transducer comprises a field-effect transistor, the voltage-to-current transducer 314 and the electrode buffer transistor 315 may be thought to form a cascode configuration. Buffering the current produced by the voltage-to-current transducer increases the input impedance of the amplifier, and/or reduces the coupling between the input of the amplifier and/or increases the bandwidth. According to an exemplary embodiment, the voltage gain through the buffer transistor is extremely high, but the current gain is close to unity (i.e. approximately 1), such that the buffered wire current $I_{wb1'}$ may be considered identical to the unbuffered wire current $I_{wb1}$, and may be referred to exchangably.

In order to multiplex the first wire current $I_{wb1}$ produced by the voltage-to-current transducer 314 (and subsequently buffered by the electrode buffer transistor 315) a first switch 316 may selectively provide the current to the connecting wire 330. Thus, the first switch controls the supply of the first wire current $I_{wb1'}$ produced by the first electrode to the shank wire 330. Similarly, a first switch of the second electrode controls the supply of a second wire current $I_{wb2}$ respectively produced by the second electrode to the connecting wire 330. Multiplexing a plurality of wire currents produced by a respective plurality of electrodes permits a single connecting wire (e.g. connecting wire 330) to a multiplexed current $I_{mux}$ to base circuitry to pass information regarding the plurality of electrodes.

There may be provided a second switch 317 in the electrode circuitry, the second switch being adapted to selectively connect the output of the buffer transistor to a second node 3182 held at a second predetermined voltage level. This allows the voltage-to-current transducer 314 to never be completely turned off, but merely switched between the integrator 342 and the second node 3182, which may provide a reduction in settling time of the transducer 314. Accordingly, this allows the time-division multiplexing to be performed at an increased speed, as the voltage on the connecting wire does not need to slew.

According to an exemplary embodiment, to improve the settling time of the transducer 314, the connecting wire is held at the second predetermined voltage level. This may be performed by a wire buffer transistor 341 positioned in the base circuitry 340. Holding the connecting wire at the second predetermined voltage level ensures that the output of the electrode circuitry is only switchable between two nodes held at the same voltage level, thus reducing the settling time and preventing any switching ripple to affect the previous stages of the circuit (for example, the voltage-to-current transducer).

Optionally, the difference between the first predetermined voltage level and the second predetermined voltage level (i.e. the voltage difference between the first node 3181 and the second node 3182) is very small, which results a reduction in power consumption.

The operation of the first switch 316 is controlled by a first control voltage $V_{con1}$, and the operation of the second switch 317 is controlled by a second control voltage. Similarly, the operation of the second electrode 320 is controlled by a respective pair of a third control voltage $V_{con3}$ and a fourth control voltage $V_{con4}$. It will be apparent that the third and fourth control voltages respectively control a first and second switch of the second electrode 320.

The features and operation of base circuitry 340 associated with the plurality of electrodes comprising a first electrode 310 and second electrode 320 shall be elucidated in the following paragraphs.

Base circuitry 340 comprises a wire buffer transistor 341, which operation has been previously described, and an integrator 342. Integrator 342 comprises the same features (that is integrating capacitor 344 and reset switch 345) and operates in the same manner as the integrator 242 described with reference to the first embodiment. For the sake of clarity, it is noted that in the present embodiment the reset switch of the integrator 342 is controlled by a reset voltage $V_{reset}$. However, for the purposes of conciseness the operation of the integrator 342 shall not be further discussed, as it largely similar to the integrator 242 of the first embodiment.

The base circuitry 340 further comprises a plurality of sampling circuits 350, 360. In the present embodiment, the base circuitry 340 comprises a first sampling circuit 350 and a second sampling circuit 360. Each sampling circuit is associated with a different electrode (for example, the first sampling circuit 350 is associated with the first electrode 310). It will be appreciated that in some example embodiments there is an equal number of sampling circuits associated with any given connecting wire (and hence integrator) as there are electrodes associated with that same connecting wire.

Sampling circuitry is used to sample-and-hold a value of the voltage output $V_{out}$ by the integrator 342. Thus a plurality of voltage values, each corresponding to a voltage detected by a respective electrode, may be held or stored at the plurality of sampling circuits.

A first embodiment of a sampling circuit shall be described with reference to the first sampling circuit 350. The second sampling circuit 360 and any further sampling circuits (not shown) typically comprises the same features and operate in the same manner.

The first sampling circuit comprises a sampling switch 351 controlled by a first sampling switch voltage $V_{sst}$. The sampling circuitry further comprises a sampling capacitor 352 and an output buffer 353. The sampling switch 351 selectively connects a first plate of the sampling capacitor to the voltage output $V_{out}$ by the integrator 342. The second plate of the sampling capacitor 352 is held at a ground voltage such that when the sampling switch is connected, the voltage across the sampling capacitor is matched to the output voltage $V_{out}$. The first plate of the capacitor 352 is also connected to an output buffer 353 having a high input impedance, such that upon disconnecting the first plate of the sampling capacitor from the output voltage, the voltage across the sampling capacitor 352 remains at the output voltage $V_{out}$. The output buffer 353 buffers the voltage across the capacitor to generate a first sampling output voltage $V_{s1}$. Such an output buffer 353 may, for example, by a known operational amplifier or transistor buffer.

It is readily understandable that the respective sampling switches of the sampling circuits may be selectively switched so as to demultiplex the voltage output $V_{out}$ into a plurality of sampling output voltages $V_{s1}$, $V_{s2}$, each corresponding to a voltage detected by an exposed surface area $V_{in1}$, $V_{in2}$ of a respective electrode 310, 320.

The second sampling circuit operates in the same manner as the first, and is controlled by a respective second sampling switch voltage $V_{ss2}$ to output a second sampling output voltage $V_{s2}$.

According to an exemplary embodiment, the sensing device may comprise any number of connecting wires, each connecting wire being associated with a set of two or more electrodes, and base circuitry comprising a respective set of two or more sampling circuits. According to an exemplary embodiment, each connecting wire is connectable to at least eight electrodes, for example at least sixteen electrodes.

An exemplary operation of the electrical circuit according to the second embodiment may be described with reference to the timing diagram exhibited in FIG. 4.

Figure 4:
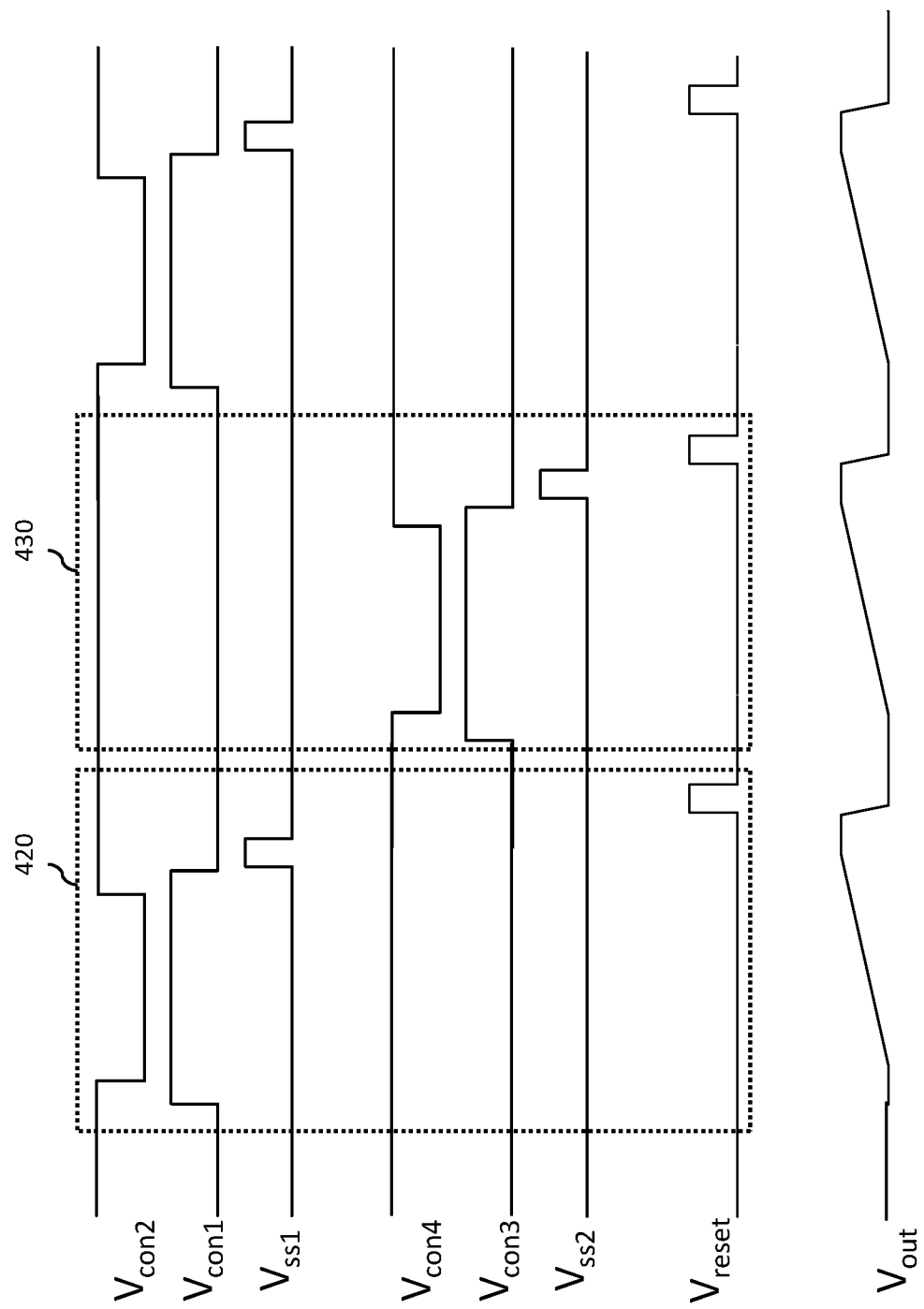
FIG. 4 illustrates an exemplary timing diagram for the electrical circuit of a sensing device according to an exemplary embodiment.

FIG. 4 identifies a first control sequence 420 to sample a first sampling voltage $V_{s2}$ from a voltage $V_{in}$ detected at the first electrode 310. Initially, the output of the first electrode is disconnected from the connecting wire 330 ($V_{con1}$ is low), but is connected to the second node 3182 held at a first predetermined voltage level ($V_{con2}$ is high). When a sample of the voltage $V_{in}$ is desired, the output of the first electrode is connected to the connecting wire 330 ($V_{con1}$ goes high) and is subsequently disconnected from the second node 3182 ($V_{con2}$ goes low). After a predetermined period of time (i.e. after the desired integration time t has elapsed), the output of the first electrode is reconnected to the second node 3182 ($V_{con2}$ goes high) and is subsequently disconnected from the connecting wire 330 ($V_{con1}$ goes low). It can be readily seen that during the time in which the output of the first electrode is connected to the connecting wire, so the output voltage $V_{out}$ (held across the integrating capacitor 344) increases.

To sample this output voltage the first sampling switch voltage is pulsed such that the voltage across the first sampling capacitor 352 is matched to the output voltage $V_{out}$. Subsequently, the voltage across the integrating capacitor 344 (the output voltage $V_{out}$) is reset by connecting then disconnecting the reset switch 345 (pulsing $V_{reset}$).

According to an exemplary embodiment, at least one of the second node 3182 or the connecting wire 330 may always be connected to the output of the electrode. Similarly, for an arbitrary electrode, the arbitrary electrode may be connected to its associated connecting wire or its associated node held at a second predetermined voltage. In other words, the timing of the first switch 316 and second switch 317 overlap, such that at least one of the first switch 316 and second switch 317 is always closed.

An identical sequence (second control sequence 430) is performed to sample a second sampling voltage $V_{s2}$ from a voltage detected at the second electrode 320. In other words, the output of the second electrode is switched from connecting to a node held at the first predetermined voltage to the connecting wire ($V_{con3}$ goes high, $V_{con4}$ goes low). After a predetermined period of time (the integration time t), this switching procedure is reversed ($V_{con4}$ goes high, $V_{con3}$ goes low). The output voltage is sampled at the second sampling circuit ($V_{ss2}$ pulses), and the voltage across the integrating capacitor 344 is reset ($V_{reset}$ pulses).

According to an embodiment, each electrode and associated sampling circuit sequentially undergoes a respective control sequence to sample a sampling output voltage associated with each electrode. In particular embodiments, the cycle of sequential control sequences is continuously repeated so as to continuously sample and measure voltages at respective electrodes.

Figure 5:
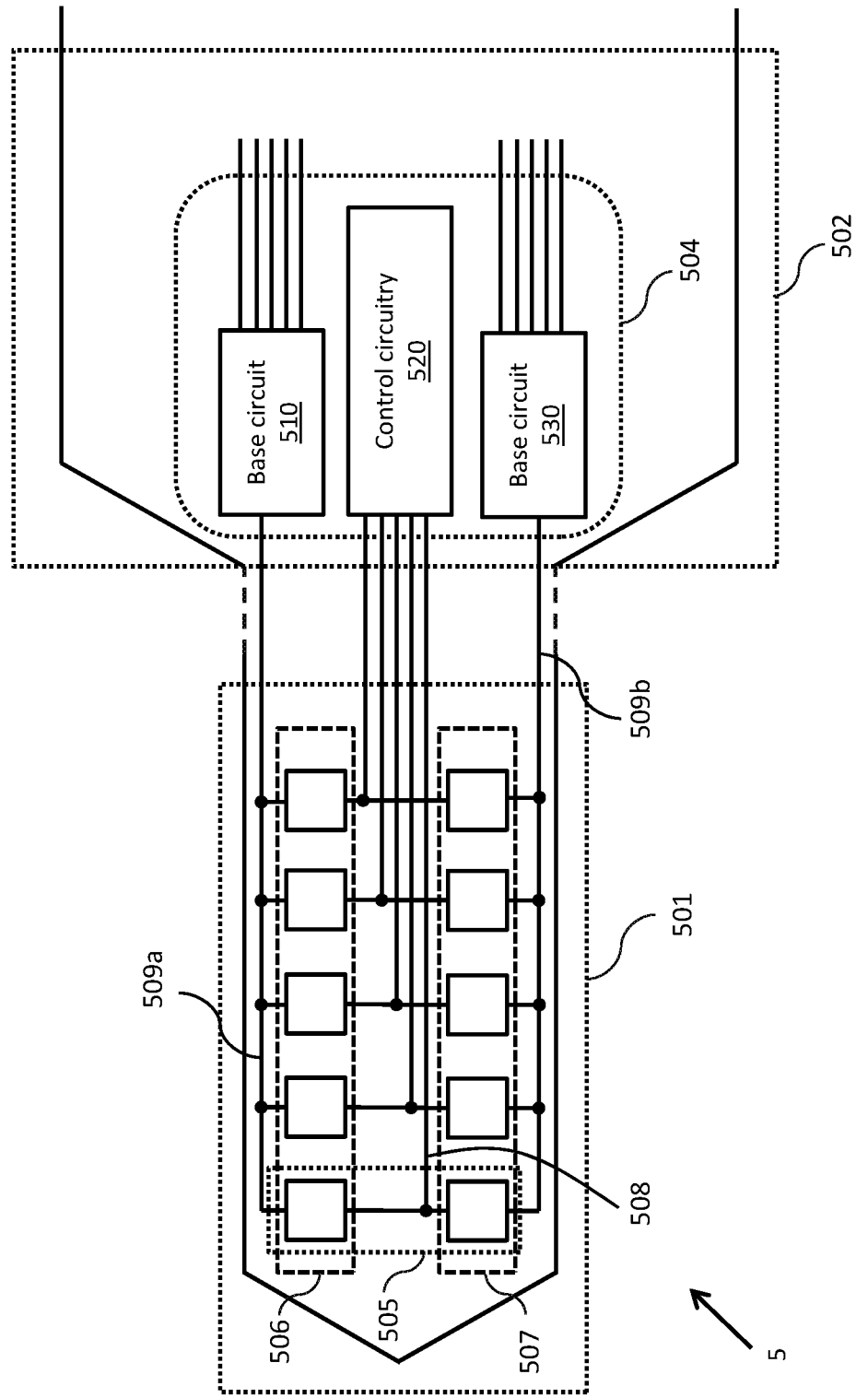
FIG. 5 depicts a sensing device according to an exemplary embodiment.

FIG. 5 depicts a sensing device 5 according to another exemplary embodiment. The sensing device 5 comprises a shank portion, or electrode area, 501 and a base portion, or output circuitry area 502. Positioned in the base 502 is base, or output circuit, electronics 504. Positioned in the shank is a first set 505 of electrodes and a second set 507 of electrodes. Each set of electrodes is connected to a respective base circuit 510, 530 in the base electronics 505 by a respective connecting wire 509a, 509b. Thus each electrode in the same set of electrodes is connected to the same base circuit, and electrodes in different sets are connected to different base circuits.

The base electronics further comprises control circuitry 520. The control circuitry is adapted to provide at least one control signal to each electrode in each set of electrodes. Any single control signal is only provided to a single electrode in any given set, but may be shared between electrodes in different sets. In an example embodiment, this may provide a reduction in the number of control lines required in the electrode area (e.g. the shank).

For example, in the present embodiment a first control signal 508 is provided to a group of electrodes 505 comprising a first electrode from the first set 506 and a first electrode from the second set 507.

It will be understood that if each set of electrodes comprises N electrodes (for example, the first set of electrode 506 comprises N electrodes when N=5) then there must be provided at least N control signals to control a single electrode from each of the sets.

In other embodiments, each electrode may receive more than one control signal (i.e. each electrode may require M control signals), for example, to control at least a first and second switch (in which case M=2). In such an embodiment there may, for example, be a plurality of sets of electrodes, each set of electrodes comprising N electrodes and each set of electrodes being associated with a different connecting wire. There may be provided a plurality of control signals equal to the number of control signals an electrode needs multiplied by the number of electrodes in a single set (i.e. M×N). Thus control signals may be shared between two or more sets of electrodes.

According to an embodiment of the invention, the sensing device as herein described may be used to perform studies, for example, both in vivo and/or in vitro.

Various other modifications will be readily apparent to those skilled in the art. For example, a skilled person would be able to substitute the above embodied P channel field-effect transistor with other suitable transducers (e.g. an N channel field effect transistor, an FET, a MOSFET, and/or a PNP/NPN transistor).

Figure 6:
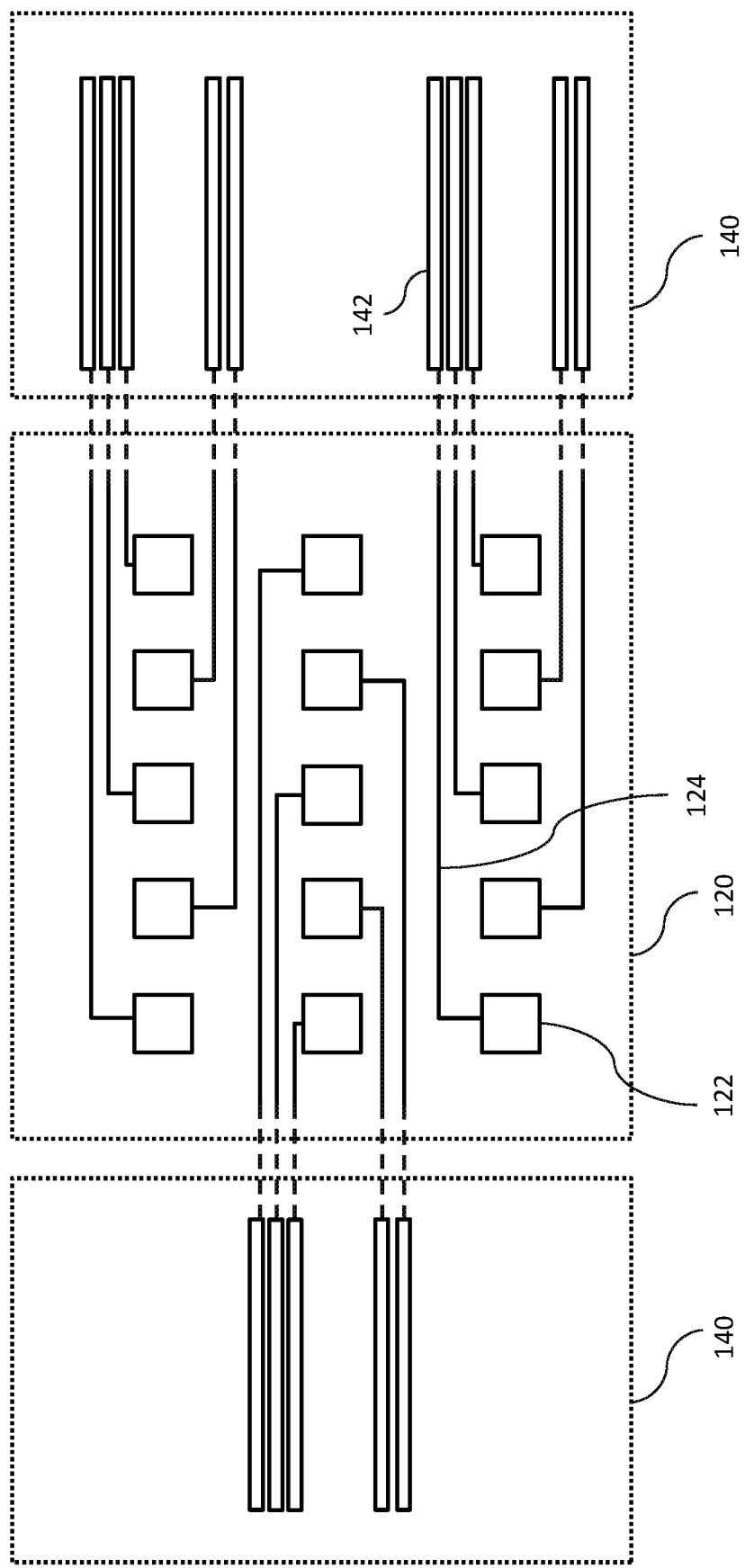
FIG. 6 depicts a sensing device according to an exemplary embodiment.

FIG. 6 depicts an exemplary embodiment of a sensing device comprising multiple microelectrode sensing arrays combined to form a high density microelectrode array for in vitro biological activity recording. According to an embodiment, multiple rows of electrodes are organized in a manner to form a two dimensional array of electrodes, e.g. multiple "shanks" are placed in a column.

The sensing device comprises an electrode (or shank) area 120 and an output circuitry (or base) area 140. The electrode area comprises at least one electrode 122 connected to an output circuit 142 of the output circuitry area 140 via a respective connecting wire 124. There are indicated (in dotted lines) optional further electrodes of the electrode area and corresponding optional output circuits of the output area. It will be readily understood by the skilled person that any number of electrodes and/or output circuits may be provided within such a sensing device.

Such a sensing device may be used, for example, for in vitro recording of cultured cells. In some embodiments, the post-processing electronics (circuits in the 'base' or output circuitry area 140) can only be placed on the edge of the array, and there may a constraint of bringing out a large number of analog signals from the electrodes on a limited number of wires to the corresponding processing circuit of the output circuit area 140, and there is a need for multiplexing multiple current-mode signals on a single line.

Further exemplary embodiments of the sensing device will be described in the following.

According to another embodiment, there is provided a deep brain implant or neural probe comprising at least one electrode each having an exposed surface area positioned on a shank. Each electrode comprises electrode circuitry adapted to convert a voltage present at the exposed surface area to a shank current. The neural probe comprises base circuitry, which is adapted to integrate a received current to generate an output voltage. The current received by the base circuitry is the shank current, passed to the base circuitry by a shank wire.

According to another embodiment, there is provided a neural probe comprising: a probe base comprising base circuitry; and a shank connected to the probe base, the shank comprising: an electrode comprising an exposed, electrically conductive, surface area and electrode circuitry connected to the exposed surface area, wherein the electrode circuitry comprises a voltage-to-current transducer adapted to produce a shank current corresponding to a voltage present at the exposed surface area; and a shank wire electrically connecting the electrode circuitry to the base circuitry, wherein the base circuitry comprises an integrator adapted to integrate the shank current so as to generate an output voltage corresponding to the shank current.

The invention claimed is:

1. A sensing device comprising:
an output area having an output circuit comprising an integrator adapted to integrate a received current so as to generate an output voltage corresponding to the received current;
an electrode area comprising:
(i) a plurality of electrodes, each electrode of the plurality of electrodes comprising an exposed, electrically conductive surface area; and
(ii) a plurality of electrode circuits connected to the exposed surface areas of the plurality of electrodes, wherein the plurality of electrode circuits comprises a plurality of voltage-to-current transducers adapted to produce respective wire currents corresponding to respective voltages present at the exposed surface areas of the plurality of electrodes; and
a connecting wire electrically connecting the plurality of electrode circuits to the output circuit,
wherein the integrator is adapted to (i) receive the respective wire currents via the connecting wire, and (ii) generate respective output voltages corresponding to the respective wire currents, and
wherein the output circuit further comprises a plurality of sampling circuits, each respective sampling circuit being associated with a different respective electrode of the plurality of electrodes, and wherein each respective sampling circuit is adapted to sample and hold the respective output voltage corresponding to the respective wire current produced by the electrode circuit connected to the respective electrode associated with the respective sampling circuit.

2. The sensing device according to claim 1, wherein each voltage-to-current transducer of the plurality of voltage-to-current transducers comprises a field-effect transistor having a gate, a drain, and a source, and wherein:
the gate of the transistor is connected to the exposed surface area; and
one of the drain or the source of the transistor is held at a first predetermined voltage level, such that a voltage at the gate of the transistor causes one of the respective wire currents to flow at the other one of the drain or the source of the transistor.

3. The sensing device according to claim 1, wherein the plurality of electrodes further comprises a plurality of high-pass filters connected between the exposed surface areas and the plurality of electrode circuits.

4. The sensing device according to claim 1, wherein the plurality of electrode circuits further comprises a plurality of electrode buffer transistors adapted to buffer the respective wire currents produced by the plurality of voltage-to-current transducers.

5. The sensing device according to claim 1, wherein:
the plurality of electrodes forms a first set of electrodes and the connecting wire is a first connecting wire;
the electrode area comprises a plurality of sets of electrodes that includes the first set of electrodes, each set of electrodes comprising at least two electrodes;
the sensing device comprises a plurality of connecting wires that includes the first connecting wire, each connecting wire being associated with a respective set of the plurality of sets of electrodes and connectable to each electrode in that respective set of electrodes; and
the wire current from each electrode in each respective set of the plurality of sets of electrodes is multiplexed using time-division multiplexing onto the associated connecting wire.

6. The sensing device according to claim 5, wherein the output area comprises a plurality of output circuits, each output circuit being connected to a different connecting wire of the plurality of connecting wires.

7. The sensing device according to claim 1, wherein each electrode circuit of the plurality of electrode circuits comprises:
an output node at which the respective wire current is defined;
a first controllable switch adapted to selectively connect the output node to the connecting wire; and
a second controllable switch adapted to selectively connect the output node to a node held at a particular predetermined voltage level.

8. The sensing device according to claim 7, wherein the output node is always connected to at least one of the connecting wire or the node held at the particular predetermined voltage level.

9. The sensing device according to claim 7, wherein each electrode circuit of the plurality of electrode circuits comprises at least one of a wire buffer transistor or other circuit components adapted to maintain the connecting wire at the particular predetermined voltage level.

10. The sensing device according to claim 7, wherein the electrode area further comprises:
a first plurality of control lines connected to control the first controllable switches of the plurality of electrode circuits; and
a second plurality of control lines connected to control the second controllable switches of the plurality of electrode circuits.

11. The sensing device according to claim 1, further comprising a flexible membrane, wherein the electrode area is formed on the flexible membrane.

12. The sensing device according to claim 11, wherein the flexible membrane is configured to be arranged on an external surface of a brain so as to detect at least one voltage present at an exterior surface of the brain.

13. The sensing device according to claim 11, wherein the flexible membrane comprises at least one of polyester, polyimide, or metallic foil.

14. The sensing device according to claim 1, wherein the plurality of electrodes are organized to form at least part of a two dimensional electrode array.

15. The sensing device according to claim 1, wherein the sensing device is a neural probe comprising a probe base and a shank connected to the probe base, and wherein the output area is formed in the probe base, and the electrode area is formed in the shank.

16. The sensing device according to claim 1, wherein the integrator comprises a controllable reset switch so as to controllably reset the output voltage.

17. The sensing device according to claim 16, wherein the integrator comprises:
   an integrating capacitor having a first plate and a second plate, the integrating capacitor being arranged so that the wire current is integrated at the first plate of the integrating capacitor to thereby generate an output voltage at the first plate, and the second plate of the integrating capacitor is held at a ground voltage; and wherein the controllable reset switch is connected between the first plate of the integrating capacitor and the second plate.

* * * * *